(12) United States Patent
Freedman et al.

(10) Patent No.: US 7,253,618 B1
(45) Date of Patent: Aug. 7, 2007

(54) METHOD FOR DETERMINING MORE ACCURATE DIFFUSION COEFFICIENT DISTRIBUTIONS OF RESERVOIR FLUIDS USING BI-POLAR PULSED FIELD GRADIENTS

(75) Inventors: Robert Freedman, Houston, TX (US); Krishnamurthy Ganesan, Sugar Land, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 11/612,715

(22) Filed: Dec. 19, 2006

(51) Int. Cl.
*G01V 3/00* (2006.01)
(52) U.S. Cl. .................... 324/303; 324/300
(58) Field of Classification Search ......... 324/300–324
See application file for complete search history.

(56) References Cited

U.S. PATENT DOCUMENTS

| | | | |
|---|---|---|---|
| 5,428,291 A | | 6/1995 | Thomann et al. |
| 5,796,252 A | | 8/1998 | Kleinberg et al. |
| 6,204,663 B1 | * | 3/2001 | Prammer ............... 324/303 |
| 6,346,813 B1 | | 2/2002 | Kleinberg |
| 6,570,382 B1 | * | 5/2003 | Hurlimann et al. ....... 324/303 |
| 6,891,369 B2 | | 5/2005 | Hurlimann et al. |
| 6,981,369 B2 | * | 5/2005 | Hurlimann et al. ....... 324/303 |
| 6,956,371 B2 | * | 10/2005 | Prammer ............... 324/303 |
| 7,053,611 B2 | | 5/2006 | Freedman |

OTHER PUBLICATIONS

Karcilek, R.F. et al., A Modified Pulsed Gradient Technique for Measuring Diffusion in the Presence of Large Background Gradients, Journal of Magnetic Resonance vol. 37, pp. 75-91, 1980.

Cotts, R.M. et al., Pulsed Field Gradient Stimulated Echo Methods for Improved NMR Diffusion Measurements in Heterogeneous Systems, Journal of Magnetic Resonance vol. 83, pp. 252-266, 1989.

Trudeau, J.D. et al., The Effect of Inhomogeneous Sample Susceptibility on Measured Diffusion Anisotropy Using NMR Imaging, Journal of Magnetic Resonance, Series B 108, pp. 22-30, 1995.

Stejskal, E.O. et al., Spin Diffusion Measurements: Spin Echoes in the Presence of a Time-Dependent Field Gradient, Journal of Chemical Physics, vol. 42, pp. 288-292, 1965.

* cited by examiner

*Primary Examiner*—Brij B. Shrivastav
(74) *Attorney, Agent, or Firm*—Martin M. Novack; Bryan L. White; Kevin P. McEnaney

(57) ABSTRACT

A method for determining a property of a substance in a downhole measurement region includes the following steps: providing a static magnetic field having a static magnetic field gradient in the measurement region; applying, in the measurement region, a pulse sequence that includes a tipping pulse, a re-focusing pulse, and a pulsed field gradient pulse train; wherein the pulsed field gradient pulse train includes a first portion and a second portion; the first portion comprising a first pulse or set of pulses having a first polarity and a second pulse or set of pulses having a second polarity, the second polarity being opposite to the first polarity, and wherein the first portion occurs before the re-focusing pulse; the second portion comprising a third pulse or set of pulses having the first polarity and a fourth pulse or set of pulses having the second polarity, and wherein the second portion occurs after the re-focusing pulse; and receiving one or more spin echoes from the measurement region.

23 Claims, 6 Drawing Sheets

| TABLE 1 | |
|---|---|
| UNI-POLAR PFG τ VALUES | APPARENT DIFFUSION CONSTANT (x $10^{-5}$) $cm^2$/ sec |
| τ = 24.3ms; POSITIVE GRADIENTS | 2.26 |
| τ = 19.3ms; POSITIVE GRADIENTS | 2.24 |
| τ = 14.3ms; POSITIVE GRADIENTS | 2.37 |
| τ = 9.3ms; POSITIVE GRADIENTS | 2.42 |
| τ = 6.3ms; POSITIVE GRADIENTS | 2.49 |
| τ = 6.3ms; NEGATIVE GRADIENTS | 2.65 |
| τ = 9.3ms; NEGATIVE GRADIENTS | 2.69 |
| τ = 14.3ms; NEGATIVE GRADIENTS | 2.87 |
| τ = 19.3ms; NEGATIVE GRADIENTS | 2.85 |
| τ = 24.3ms; NEGATIVE GRADIENTS | 2.85 |

| TABLE 2 | |
|---|---|
| BIPOLAR PFG PARAMETERS | DIFFUSION CONSTANT (x $10^{-5}$) $cm^2$/ sec |
| $\tau$ = 16.25ms; GRADIENTS = + - + - | 2.50 |
| $\tau$ = 17.25ms; GRADIENTS = - + - + | 2.53 |
| $\tau$ = 17.25ms; GRADIENTS = + - + - | 2.52 |
| $\tau$ = 21.25ms; GRADIENTS = + - + - | 2.50 |
| $\tau$ = 26.25ms; GRADIENTS = + - + - | 2.54 |
| $\tau$ = 31.25ms; GRADIENTS = + - + - | 2.51 |

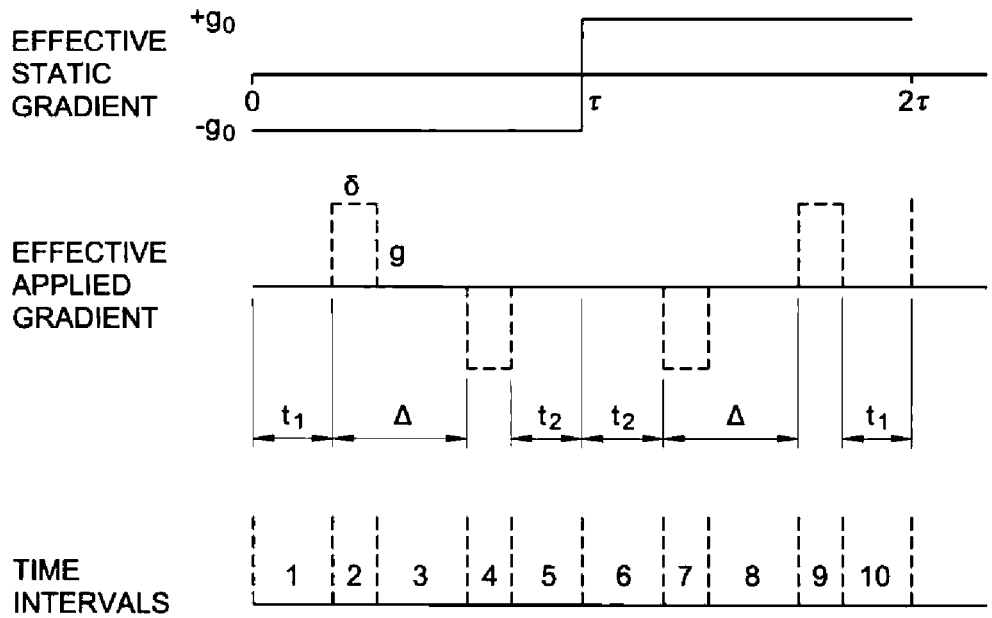

*Fig. 8*

| TABLE 3 | | | |
|---|---|---|---|
| STEPS | TIME INTERVAL | EFFECTIVE GRADIENT ($G_{eff}$) | $\int_0^t G_{eff}\, dt$ |
| 1 | $0 \to t_1$ | $-g_0$ | $-g_0 t$ |
| 2 | $t_1 \to t_1 + \delta$ | $g - g_0$ | $-g_0 t + g(t - t_1)$ |
| 3 | $t_1 + \delta \to t_1 + \Delta$ | $-g_0$ | $-g_0 t + g\delta$ |
| 4 | $t_1 + \Delta \to t_1 + \Delta + \delta$ | $-g_0 - g$ | $-g_0 t - g(t + t_2 - \tau)$ |
| 5 | $t_1 + \Delta + \delta \to \tau$ | $-g_0$ | $-g_0 t$ |
| 6 | $\tau \to \tau + t_2$ | $g_0$ | $-g_0(t - 2\tau)$ |
| 7 | $\tau + t_2 \to \tau + t_2 + \delta$ | $g_0 - g$ | $g_0(t - 2\tau) - g(t - \tau - t_2)$ |
| 8 | $\tau + t_2 + \delta \to \tau + \Delta + t_2$ | $g_0$ | $g_0(t - 2\tau) - g\delta$ |
| 9 | $\tau + \Delta + t_2 \to \tau + \Delta + t_2 + \delta$ | $g_0 + g$ | $g_0(t - 2\tau) + g(t - \tau - t_2 - \Delta + \delta)$ |
| 10 | $\tau + \Delta + t_2 + \delta \to 2\tau$ | $g_0$ | $g_0(t - 2\tau)$ |

*Fig. 9*

| TABLE 4 | | |
|---|---|---|
| STEP | $g_0^2$ COEFFICIENTS | $g^2$ COEFFICIENTS |
| 1 | $1/3 \ t_1^3$ | 0 |
| 2 | $1/3 \ [(t_1 + \delta)^3 - t_1^3]$ | $(1/3) \delta^3$ |
| 3 | $1/3 \ [(t_1 + \Delta)^3 - (t_1 + \delta)^3]$ | $\delta^2 (\Delta - \delta)$ |
| 4 | $1/3 \ [(t_1 + \Delta + \delta)^3 - (t_1 + \Delta)^3]$ | $(1/3) \delta^3$ |
| 5 | $1/3 \ [\tau^3 - (\tau - t_2)^3]$ | 0 |
| 6 | $1/3 \ [(t_2 - \tau)^3 + \tau^3]$ | 0 |
| 7 | $1/3 \ [(t_2 + \delta - \tau)^3 - (t_2 - \tau)^3]$ | $(1/3) \delta^3$ |
| 8 | $1/3 \ [(\Delta + t_2 - \tau)^3 - (t_2 + \delta - \tau)^3]$ | $\delta^2 (\Delta - \delta)$ |
| 9 | $1/3 \ [(t_1 + \delta)^3 - t_1^3]$ | $(1/3) \delta^3$ |
| 10 | $1/3 \ t_1^3$ | 0 |

Fig. 10

| TABLE 5 | |
|---|---|
| STEP | $g \ g_0$ COEFFICIENTS |
| 1 | 0 |
| 2 | $(-2/3) \delta^3 - t_1 \delta^2$ |
| 3 | $-\delta \ [(t_1 + \Delta)^2 - (t_1 + \delta)^2]$ |
| 4 | $(2/3) \delta^3 + \delta^2 (t_1 + \Delta) - \delta(t_1 + \Delta + \delta)^2 + \delta (t_1 + \Delta)^2$ |
| 5 | 0 |
| 6 | 0 |
| 7 | $(-2/3) \delta^3 - (t_2 - \tau) \delta^2$ |
| 8 | $-\delta \ [(\Delta + t_2 - \tau)^2 - (t_2 + \delta - \tau)^2]$ |
| 9 | $(2/3) \delta^3 - (t_1 + \delta) \delta^2 - \delta \ [-(t_1 + \delta)^2 + t_1^2]$ |
| 10 | 0 |

Fig. 11

METHOD FOR DETERMINING MORE ACCURATE DIFFUSION COEFFICIENT DISTRIBUTIONS OF RESERVOIR FLUIDS USING BI-POLAR PULSED FIELD GRADIENTS

BACKGROUND OF THE INVENTION

Field of the Invention

This invention relates to methods for determining properties of substances, such as formation fluids, in downhole measurement regions, using nuclear magnetic resonance.

The introduction of pulsed nuclear magnetic resonance (NMR) logging tools in the early 1990s has provided the oil and gas industry with powerful new methods for evaluating petroleum reservoirs. The initial applications of pulsed NMR logging tools were aimed at providing important rock-quality properties such as lithology-independent total porosity, free-and bound-fluid porosity, and permeability.

As is well known, the rate of decay of the NMR signal can be described, for example, by a distribution of decay times, $T_2$s, which are called transverse relaxation times. It is customary to fit the measured NMR signals to a sum of several decaying single-exponential signals, each with amplitude $A(T_2)$ and associated decay time $T_2$. The fitting procedure is achieved by a mathematical technique known as inversion. The amplitudes $A(T_2)$ are outputs of the inversion procedure.

The measurement of diffusion has become an important function of NMR well logging devices. NMR signals are attenuated by the molecular diffusion of oil, gas, and brine molecules. This effect is the physical mechanism that underlines all stand-alone NMR fluid-characterization methods. Molecular diffusion is the random motion of molecules. The molecular diffusion constant of a molecule determines the mean square distance that the molecule will move per unit time. The diffusion of gas and water molecules can be described by a single molecular diffusion constant. Crude oils, on the other hand, have distributions of molecular diffusion constants that reflect the diversity of molecular sizes among the various components. Small lightweight molecules like methane and ethane are relatively mobile in the gas phase and have molecular diffusion constants (D) that are typically about an order of magnitude greater than those of water molecules. In contrast, intermediate-to-high-viscosity crude oils have molecular diffusion constants that are much smaller than those of water. Contrasts in the molecular diffusion constants of formation fluids are exploited by using specially designed NMR measurements that are sensitive to diffusion. The NMR data are then analyzed to provide oil, gas, and brine saturations.

The U.S. Pat. No. 7.053,611 (hereinafter sometimes referred to as the '611 Patent) of R. Freedman, is assigned to the same assignee as the present Application, and is incorporated herein by reference. The '611 Patent discloses, inter alia, a method that includes acquiring a suite of nuclear magnetic resonance (NMR) measurements of a fluid sample using a pulse sequence that includes pulsed field gradient (PFG) pulses for encoding diffusion information, wherein each NMR measurement in the suite is acquired with a different value in a parameter in the pulsed field gradient pulses for producing a different diffusion effect. The suite of NMR measurements is inverted to produce a distribution function that relates diffusion properties of the fluid sample with an NMR property of the fluid sample; for example, the longitudinal and/or transverse magnetic relaxation time thereof. The '611 Patent discloses, in one embodiment, the use of uni-polar pulsed field gradient CPMG sequences for measuring relaxation time and translational diffusion distributions of sampled fluids in the flowline of a fluid sampling well logging tool.

The technique of the '611 Patent assumes that the static field gradient can be neglected by using a permanent magnet with a substantially homogeneous magnetic field. When static field gradients are present, errors are encountered in the determination of diffusion constants. The '611 Patent proposes a solution to the problem caused by static field gradients by using bi-polar pulse sequences such as those developed by Karlicek and Lowe ("A Modified Pulsed Gradient Technique for Measuring Diffusion in the Presence of Large Background Gradients," in J. of Mag. Res., v. 37, p. 75-91, 1980). The bi-polar pulse sequence proposed by Karlicek and Lowe is unnecessarily complex and poorly suited for measuring small diffusion constants and relaxation times in viscous oils. For example, it has a 90-degree excitation pulse followed by five 180-degree re-focusing pulses at times $\tau$, $3\tau$, $5\tau$, $7\tau$, and $9\tau$. Gradient pulses of duration $2\tau$ with symmetrical polarities of plus, minus, minus, and plus are applied in between the four pairs of successive 180-degree pulses. The diffusion-encoded echo in the Karlicek and Lowe pulse sequence occurs after a long echo time, i.e, $10\tau$. This is problematic because the short relaxation time components of viscous oils have already decayed by the time the first echo is observed and, therefore, these components cannot be measured using the Karlicek and Lowe pulse sequence.

The '611 Patent also refers to a bi-polar PFG pulse sequence proposed by Cotts, et al. ("Pulsed Field Gradient Stimulated Echo Methods for Improved NMR Diffusion Measurements in Heterogeneous Systems," in J. of Mag. Res. v. 83, p. 252-266, 2989) as a means for eliminating the product of the static and applied gradient cross term. The Cotts et al. bi-polar sequences are based on "stimulated echo pulse sequences" which result in a 50% signal loss. The 50% signal loss is objectionable since having high signal-to-noise ratio reduces the measurement time, which is a very important consideration in well logging operations.

Bi-polar PFG sequences have been used in medical imaging applications for measuring diffusion in heterogeneous laboratory samples in which the applied magnetic field is very homogeneous (as above noted), but produces internal gradients because of the nature of the material of the sample. Reference can be made, for example to Trudeaux et al., J. of Magnetic Resonance, Series B, vol. 108, pp. 22-30, 1995, which discussed a bi-polar PFG sequence as a means for removing the effects of internal gradients on diffusion of water measured in pig spinal cords and celery stalks.

Thomann et al. in U.S. Pat. No. 5,428,291 propose using bi-polar stimulated echo pulse sequences to study fluid flow in porous media. The U.S. Pat. No. 5,796,252 also treats bi-polar PFG sequences. The '252 Patent discusses using bi-polar PFG pulse sequences to measure diffusion and relaxation of reservoir fluids in the pore spaces of earth formations surrounding a borehole. The '252 Patent cites academic publications on stimulated echo bi-polar sequences. The '252 Patent teaches that the stimulated echo bi-polar pulse sequences could be used to mitigate the effect of internal gradients induced in the pore spaces of heterogeneous porous rock formations by the static magnetic field. As noted above, stimulated echo sequences are generally objectionable because they compromise signal-to-noise ratio without offering a clear advantage justifying the loss of signal.

U.S. Pat. No. 6,891,369 discusses pulse sequences for measuring diffusion and relaxation times in a fluid sampling tool. The '369 Patent discloses pulse sequences for measuring diffusion in the presence of a static magnetic field gradient and also pulse sequences using PFG sequences. The '369 Patent does not address the problem of cancelling the product of the static and applied field gradient cross term to obtain more accurate diffusion constants using PFG sequences.

There is a need for a method that can provide more accurate diffusion constants by cancelling the product of the static and applied gradient cross-term (to be described further hereinbelow) which otherwise causes systematic errors in measured diffusion properties. Moreover, there is a need for a relatively simple RF pulse sequence that encodes diffusion information in an echo that is detected after only a single re-focusing pulse, i.e., early in time before the short relaxation time components are completely lost by T2 decay.

SUMMARY OF THE INVENTION

In accordance with a feature of embodiments of the present invention, corrective pulses are applied in a pulse sequence to obtain cancellation of a component of the spin echoes that depends on the magnitude and direction of the static magnetic field gradient of the static magnetic field.

A form of the invention has application for use in conjunction with a logging device downhole in an earth borehole. A method is set forth for determining a property of a substance in a downhole measurement region, including the following steps: providing a static magnetic field having a static magnetic field gradient in the measurement region; applying, in the measurement region, a pulse sequence that includes a tipping pulse, a re-focusing pulse, and a pulsed field gradient pulse train; wherein the pulsed field gradient pulse train includes a first portion and a second portion; the first portion comprising a first pulse or set of pulses having a first polarity and a second pulse or set of pulses having a second polarity, the second polarity being opposite to the first polarity, and wherein the first portion occurs before the re-focusing pulse; the second portion comprising a third pulse or set of pulses having the first polarity and a fourth pulse or set of pulses having the second polarity, and wherein the second portion occurs after the re-focusing pulse; and receiving one or more spin echoes from the measurement region.

In an embodiment of the invention, the measurement region can comprise a sample chamber in said logging device, the sample chamber containing fluid from formations surrounding the earth borehole. The measurement region can alternatively comprise a region of formations surrounding the earth borehole, or can comprise a region in the earth borehole itself.

In an embodiment of the invention, the step of determining said property from said spin echoes comprises inverting to determine a diffusion constant, or a plurality of diffusion constants, of said substance. The inversion can also determine a plurality of magnetic relaxation times of said substance. In a form of this embodiment, a correction factor is applied in the inversion for the square of the static gradient of said static magnetic field. The correction factor can be determine empirically beforehand.

Further features and advantages of the invention will become more readily apparent from the following detailed description when taken in conjunction with the accompanying drawings.

BRIEF DESCRIPTION OF THE DRAWINGS

FIG. 8 shows graphs which help illustrate gradient components in each of the 10 illustrated time intervals which are the sum of the applied (g) and static ($g_o$) field gradients.

FIG. 9 shows Table 3, which is a table presenting effective gradients in column 3 and their time integrals in column 4, for each of the 10 time intervals shown in column 2.

FIG. 10 shows Table 4, which is a table presenting coefficients of the squares of the static and applied magnetic field gradients in each time interval found from performing the double integration in Eq. 5.

FIG. 11 shows Table 5, which is a table presenting coefficients of the product of the static and applied magnetic field gradients in each time interval found from performing the double integration in Eq. 5.

DETAILED DESCRIPTION

Embodiments of the method hereof can be practiced in conjunction with downhole logging apparatus employed in wireline logging equipment, formation testing equipment, and/or logging-while-drilling equipment. One exemplary embodiment determines reservoir fluid properties using an NMR module in a downhole tool, such as a fluid sampling tool disclosed in U.S. Pat. No. 6,346,813. An example of formation fluid tester tool is the Modular Formation Dynamics Testing tool marketed under the trade name of MDT™ by Schlumberger Technology Corp. (Houston, Tex.). The present invention may test fluids within the borehole, fluids within a sample chamber disposed in the borehole, and fluids in the formation as well.

Figure 1:
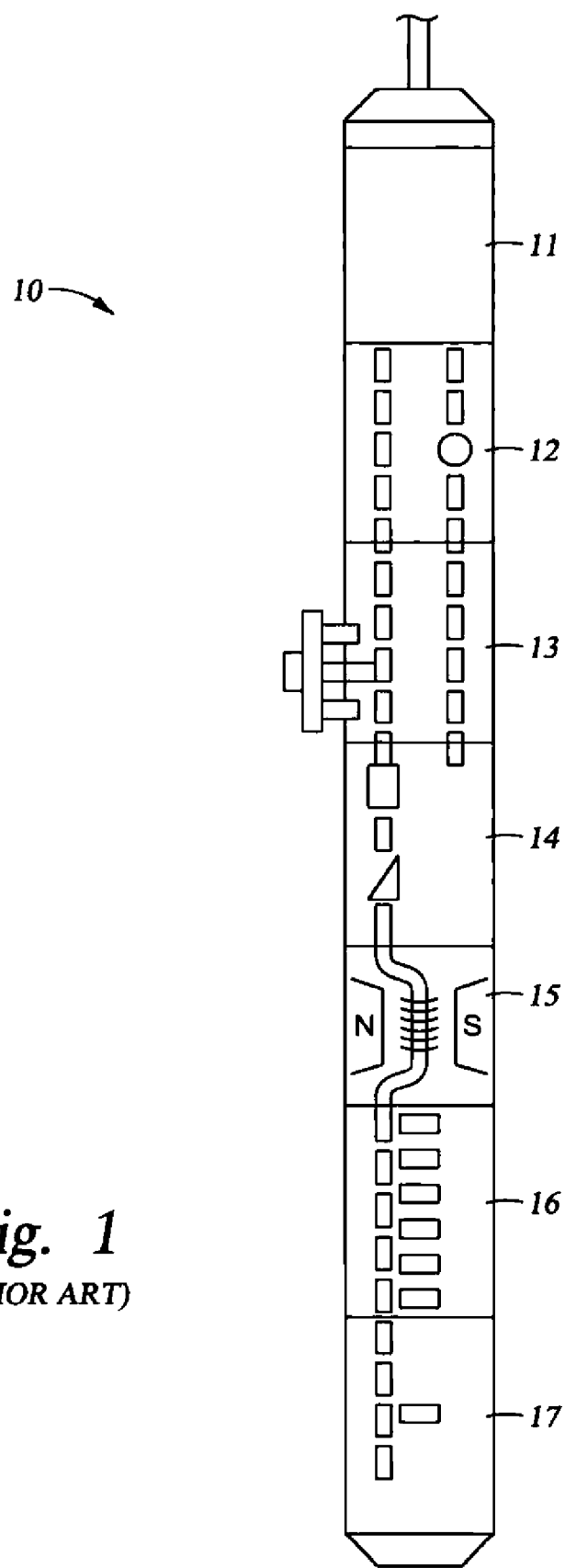
FIG. 1 shows a prior art formation testing (or sampling) logging device having an NMR module.

FIG. 1 shows an exemplary formation fluid testing (or sampling) tool 10 (e.g., an MDT™ tool) that is described, for example, in U.S. Pat. No. 7,053,611, and includes the following modules: an electronic module 11, which may include a processor and a memory; a hydraulic power module 12; a probe module 13, which may be deployed to make a hydraulic seal with the formation; a pumpout module 17; an optical fluid analyzer (OFA) 14; an NMR module 15, and a multisample module 16. The logging tool 10 can be suspended in an earth borehole on an armored multiconductor cable, the length of which substantially determines the depth of the tool. Equipment (not shown) at the earth's surface can include control and communication circuitry for the logging apparatus. The surface equipment can typically include a processor and a recorder. These may all generally be of known type. Although the control and processing associated with embodiments hereof may be performed by downhole and uphole processors, it will be understood that parts of the processing may be performed at locations remote from the borehole, which may be in direct or indirect communication with the wellsite. Also, while preferred embodiments hereof are described in the context of wireline logging equipment, it will be understood that the invention can also have application to logging while drilling, tripping, and/or pausing, or other investigation in an earth borehole.

The NMR module 15 of this embodiment includes an NMR sensor of a type disclosed in the above-referenced U.S. Pat. No. 7,053,611, which is incorporated herein by reference. The NMR sensor includes a permanent magnet that can produce a substantially homogeneous static magnetic field over the volume of the fluid sample. In addition, the NMR sensor includes at least one coil that can produce pulsed field gradients (PFG) of defined strengths and durations across the sample volume. As described in the '611 Patent, a homogeneous static magnetic field in combination with a pulsed magnetic field gradient can provide measurements with better signal-to-noise ratios because a larger sample volume is resonated, as compared to a static magnetic field having a static field gradient, which can only induce a small portion of the sample (a "sample slice") to resonate. The NMR sensor also includes a coil (an RF antenna) for producing radio frequency (RF) magnetic field pulses. The magnetic moment of the RF antenna is substantially perpendicular to the magnetic moment of the static magnetic field.

Figure 2:
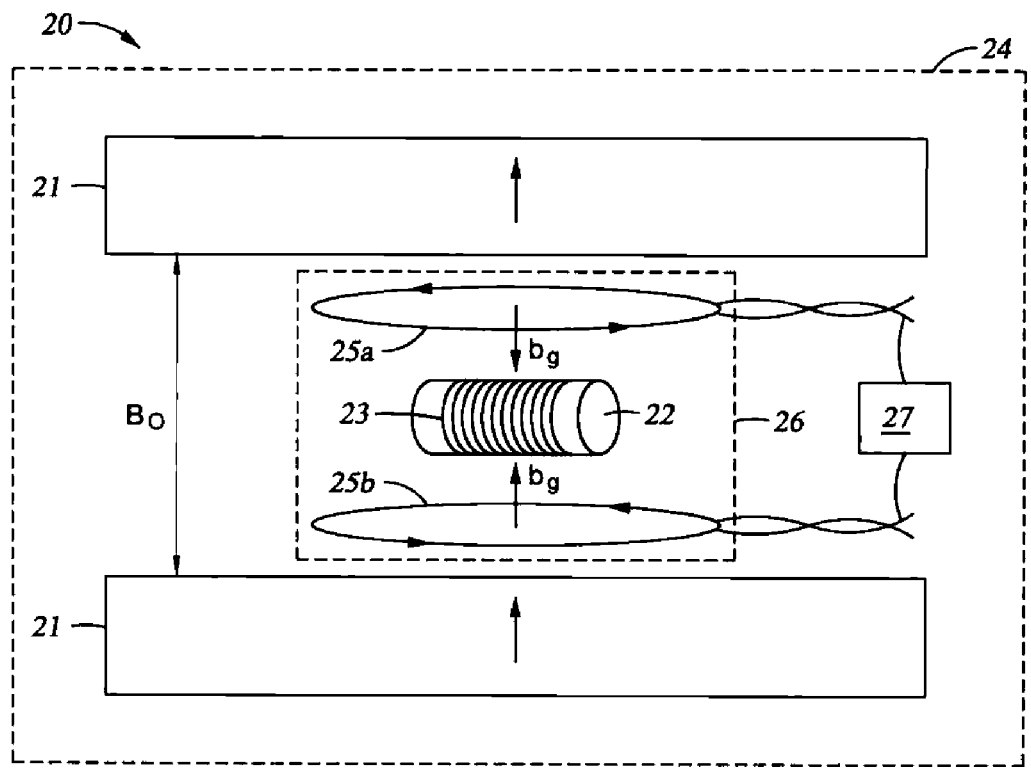
FIG. 2 shows a prior art NMR sensor of a type described in U.S. Pat. No. 7,053,611.

FIG. 2 shows an NMR sensor as disclosed in the '611 Patent. As shown in FIG. 2, and described in the '611 Patent, the NMR sensor 20 includes a magnet 21 (e.g., a permanent magnet) that is designed to produce a substantially homogeneous magnetic field ($B_0$) in a sample volume 22. The permanent magnet 21 may be made of Samarium Cobalt or any other suitable material. The permanent magnet 21, which may comprise a single piece or several pieces that surround the sample volume 22, may further include permeable pole pieces attached to its surfaces for shaping the magnetic field and for reducing the magnetic field gradient in the sample region so that the static field is substantially homogeneous over the sample volume (sample chamber) 22.

As further described in the '611 Patent, in some embodiments the sample volume 22 may be configured to connect to a formation fluid flow line so that the sensor 20 may be used to measure or monitor the properties of fluid flowing through the sample volume (sample chamber) 22. An RF antenna (coil) 23 surrounds the sample volume 22. The RF antenna 23 is designed to radiate an oscillating radiofrequency (RF) magnetic field ($B_1$) having a magnetic moment substantially perpendicular (orthogonal) to that of the static magnetic filed produced by the permanent magnet 21. The RF antenna 23 may comprise a solenoid coil, a saddle coil, or any other suitable coil. The same RF antenna 23 may function as a transmitter to transmit the oscillating magnetic field and as a receiver to receive the signals, as disclosed in U.S. Pat. No. 6,346,813. Alternatively, separate transmitter and receiving antennas may be used.

As further described in the '611 Patent, the NMR sensor 20 shown in FIG. 2 also includes two gradient coils 25a and 25b that are configured to produce magnetic field gradients across the volume of the sample 22. The gradient coils 25a and 25b are connected to a control unit 27 that can energize the gradient coils 25a and 25b at a selected strength for a predetermined duration. While two gradient coils 25a and 25b are shown, one or more gradient coils may be used. During the duration of a gradient pulse, opposing magnetic fields $b_q$ may be created to induce a magnetic field gradient g over the sample volume. The sensor 20 may be protected and supported by a casing 24. The casing 24 may be made of a magnetic steel with high magnetic permeability for confining the magnetic field $B_0$ and for providing strength to the assembly. A shield 26 can be employed to separate the RF antenna 23 and the permanent magnet 21. The shield may be made of a material (e.g., copper) that can prevent the oscillating RF field produced by the RF antenna 23 from interacting with the permanent magnet 21 so that magnetoacoustic ringing in the magnet can be minimized.

As further described in the '611 Patent, the NMR sensor thereof can be used to make measurements related to the diffusion and relaxation properties of fluid samples.

Although the static magnetic field produced by the type of device shown in FIG. 2 is almost homogeneous, it is difficult, if not impossible, to produce a truly homogeneous static magnetic field, and at least a relatively small static field gradient (i.e., relatively small with respect to the average magnitude of the static field) will generally be present.

Figure 3:
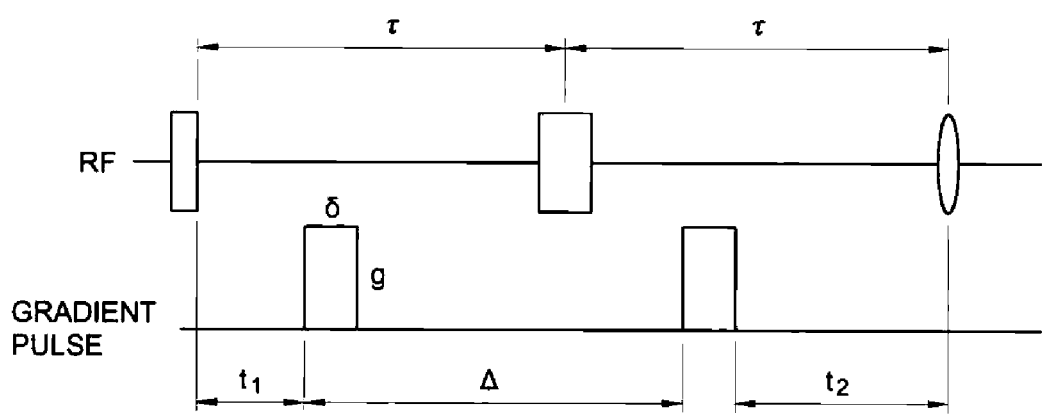
FIG. 3 shows a PFG spin-echo pulse sequence used, for example, in laboratory instruments, with homogeneous static magnetic fields, to measure diffusion in liquid samples.

Stejskal and Tanner, in the Journal of Chemical Physics, v. 42, no. 1, 288-292, 1965, proposed the type of uni-polar PFG pulse sequence shown in FIG. 3. This is a pulse sequence widely used in laboratory NMR instruments for measuring molecular diffusion in liquids. Accurate measurements are possible because laboratory instruments have magnets that produce very homogeneous (e.g., to within a few parts per million) magnetic fields. In the presence of a static magnetic field gradient, an equation for the amplitude of the echo at time $2\tau$ was derived by Stejskal and Tanner as shown in Eq. 1.

$$M(2\tau) = M_0 \exp\left(-\frac{2\tau}{T_2}\right)\exp(-A)\exp(-B), \quad \text{where,} \tag{1}$$

$$A = \gamma^2 D\left\{\frac{2}{3}\tau^3 g_0^2 + g^2\delta^2\left(\Delta - \frac{1}{3}\delta\right)\right\}, \quad \text{and,} \tag{2}$$

$$B = -\gamma^2 D\delta\left\{(t_1^2 + t_2^2) + \delta(t_1 + t_2) + \frac{2}{3}\delta^2 - 2\tau^2\right\}\bar{g}\cdot\bar{g}_b. \tag{3}$$

In the above equations $M_0$ is the equilibrium magnetization, $T_2$ is the spin-spin relaxation time, $g_0$ is the amplitude of the static field gradient, $\gamma$ is the gyromagnetic ratio of the nuclear spin, D is the diffusion constant, and the variables $\delta$, $\Delta$, $\tau$, $t_1$, and $t_2$ are times indicated in FIG. 3. As is conventional, the first RF pulse is a 90 degree tipping pulse and the second RF pulse is a 180 degree refocusing pulse, followed by a spin echo. Typically, additional spin echoes are produced after further refocusing pulses. The echo amplitude in Eq. 1 depends not only on the amplitude of the applied gradient strength (g) and the amplitude of static gradient ($g_0$) but also on the scalar product of the applied and static gradient vectors (referred to as the cross term) as can be seen from Eq. 3. It is the dependence on the direction (e.g., in addition to its magnitude) of the static field gradient that leads to systematic errors in diffusion constants measured using the type of PFG sequence shown in FIG. 3. Note that the cross term effect depends on the echo time (2τ).

An embodiment of the invention employs a bi-polar PFG sequence that is a modification of the sequence shown in FIG. 3. The bi-polar sequence of this embodiment involves application of a gradient pulse of opposite polarity following each of the gradient pulses shown in FIG. 3. As described below, both experiment and calculations demonstrate that for this bi-polar PFG sequence the contribution from the scalar product of the applied and static gradient vectors is absent. Moreover, it is shown that by using this bi-polar PFG sequence, accurate diffusion constants can be derived even in the presence of a static magnetic field gradient. It should be pointed out that even with the bi-polar PFG hereof there remains a static gradient effect identical to that in the first term of Eq. 2. However this term does not pose a problem because the squared amplitude of the static gradient can be measured by NMR diffusion measurements made, for example, on water samples in the static gradient (i.e., without using PFG measurements) of the inhomogeneous magnetic field. Since one knows the squared amplitude of the static field gradient, it can be input into the model used to invert the bi-polar PFG data.

Figures 4, 5:
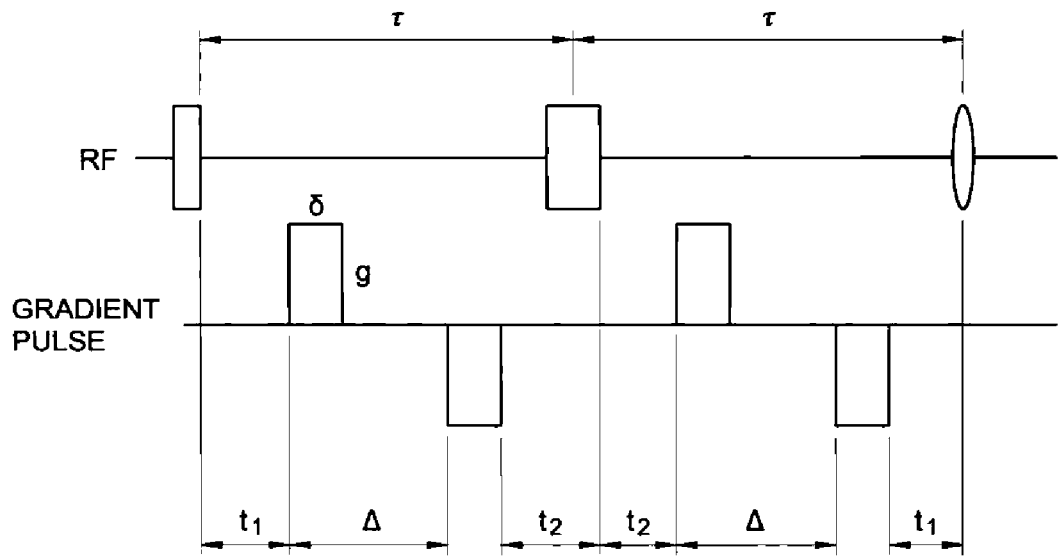
FIG. 4 shows a PFG spin-echo pulse sequence with an asymmetrical sequence of PFG pulse polarities in accordance with an embodiment of the invention, for measuring accurate diffusion in the presence of a static magnetic field gradient.
FIG. 5 shows Table 1, which is a table of apparent diffusion constants of water derived from uni-polar PFG spin-echo sequences that were acquired using a quasi-homogeneous NMR magnet.

The bi-polar PFG sequence in FIG. 4 is a preferred embodiment of an NMR pulse sequence for making accurate molecular diffusion constant measurements in the flowline of a fluid sampling well logging tool. It should be noted that a train of re-focusing RF pulses may be applied following the echo shown in FIG. 4. The RF pulses produce a train of spin-echoes that provide information on spin-spin relaxation. Such sequences are referred to as PFG-CPMG sequences. By acquisition of a suite of bi-polar sequences having different polarization times and gradient pulse parameters, one can derive multi-dimensional distributions (functions of $T_1$, $T_2$, and D) as discussed in the '611 patent.

It is shown below in a later section that the bi-polar PFG spin-echo amplitude, $M(2\tau)$, is given by the equation, $$M(2\tau) = M_0 \exp\left(-\frac{2\tau}{T_2}\right) \exp\left(-\gamma^2 D\left\{\frac{2}{3}\tau^3 g_0^2 + 2\delta^2\left(\Delta - \frac{1}{3}\delta\right)g^2\right\}\right). \quad (4)$$

Note that spin-echo amplitude in Eq. (4) does not exhibit the troublesome dependence on the scalar product of the applied and pulsed field gradient vectors seen in Eq. 3. The bi-polar PFG spin-echo sequence shown in FIG. 4 completely eliminates this cross coupling between the static and the applied magnetic field gradients. It is this coupling term that leads to systematic errors in diffusion constants measured using the PFG method in inhomogeneous static magnetic fields. Equations 1 and 4 are almost identical except for the cross coupling term. The only difference, aside form the cross term, is the extra factor of two that multiplies $g^2$ in the argument of the exponential function in Eq. 4. Accordingly, it will be understood that the bi-polar PFG spin-echo sequence shown in FIG. 4 can be used to measure diffusion more accurately than uni-polar sequences using an NMR magnet that has a inhomogeneous static magnetic field.

The section that follows provides experimental verification of the problems caused by the static gradient cross coupling effect even for a quasi-homogeneous (i.e., a magnet with a relatively small static gradient) NMR magnet. PFG diffusion measurements were conducted using a quasi-homogeneous magnet designed for use in a downhole fluid sampling tool. A suite of uni-polar PFG measurements were acquired to determine the magnetite of the cross coupling effect on the measured diffusion constants of water samples. The uni-polar PFG sequences were acquired with the two gradient pulses both having either positive or negative polarity. The two gradient pulse polarities correspond to plus or minus algebraic signs of the applied gradient (g). The differences in the echo amplitudes observed using the two polarities are solely caused by the cross coupling term. That is, in the absence of the cross coupling term, one would derive the correct diffusion constants irrespective of the polarity of the uni-polar PFG pulses. For each polarity (positive or negative) of the applied gradient a suite of uni-polar PFG diffusion measurements was acquired with pulse durations (δ) of 200, 400, 600, 800, 1000, 1300, 1600, and 2000 microseconds. The complete suite of pulse durations was acquired for each of five different echo times (2τ) equal to 12.6, 18.6, 28.6, 38.6, and 48.6 milliseconds. The water diffusion constants determined from these measurements are shown in Table 1 of FIG. 5. The second column of the table shows the apparent diffusion constants derived from uni-polar PFG sequences using positive and negative polarity pulses. The differences in diffusion constants seen in Table 1 are caused by the cross coupling between the static and applied magnetic field gradient. Since one does not know the direction of the static field gradient, the cross coupling could not be included in the analysis. Note that both polarities provide different and also incorrect water diffusion constants, which also show a non-physical dependence on the echo spacing which is caused by the cross coupling.

Figures 6, 7:
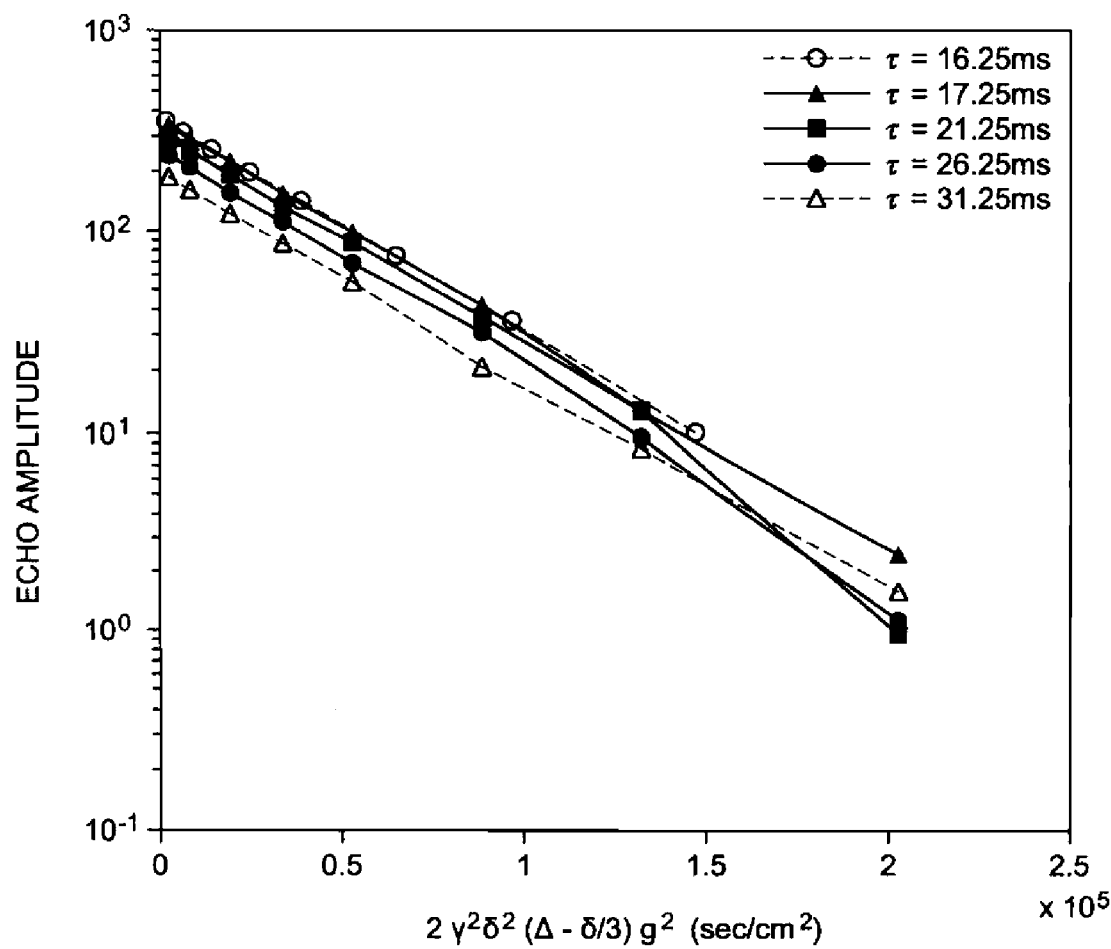
FIG. 6 is a plot of spin-echo amplitudes versus pulse durations ($\delta$) for five different values of echo spacings ($2\tau$). It can be observed that the slopes of the lines are approximately equal for the different echo spacings as predicted by theory. The deviations from linearity for two of the echo times (i.e., 42.5 and 52.5 ms) at the longest value of $\delta$ are caused by low signal-to-noise ratios.
FIG. 7 shows Table 2, which is a table of apparent diffusion constants of water derived from bi-polar PFG spin-echo sequences that were acquired using a quasi-homogeneous NMR magnet.

The uni-polar PFG experiments just described established that the cross coupling term cannot be neglected, even for quasi-homogeneous magnets and relatively large pulsed field gradients. Bi-polar PFG measurements using the spin-echo sequence shown in FIG. 4 were conducted to determine if accurate water diffusion constants can be derived using the quasi-homogeneous NMR magnet described above. The NMR sensor (i.e., magnet, RF and gradient coils) described above was also used to perform bi-polar PFG spin-echo measurements. A custom designed bi-polar circuit suitable for downhole operation was used to generate the bi-polar PFG sequences. A suite of bi-polar PFG spin-echo measurements was acquired with pulse durations (δ) equal to 200, 400, 600, 800, 1000, 1300, 1600, and 2000 microseconds. The complete suite of pulse durations was acquired for each of five different echo times (2τ) equal to 32.5, 34.5, 42.5, 52.5, and 62.5 ms. The diffusion time (Δ) was equal to 8.0 ms for all of the aforementioned echo times except for the echo time of 34.5 ms for which it was 6.0 ms. The observed spin-echo amplitudes are shown on a semi-log plot in FIG. 6 as a function of the pulse durations for the five different echo times. As can be seen from Eq. 4, the slopes of the lines provide five estimates of the apparent water diffusion constants, which are shown in Table 2 of FIG. 7. There is an additional entry in Table 2 that corresponds to the bi-polar sequence with the polarities of the four gradient pulses shown in FIG. 4 reversed. This bi-polar pulse sequence is invariant if the polarities of the 4 gradient pulses in the sequence are reversed. The important requirement is that the polarities of the four gradient pulses be anti-symmetrical with respect to the re-focusing RF pulse. The apparent diffusion constants in Table 2 are consistent with one another and with the value expected for water (i.e., approximately 2.5 cm$^2$/s) at a temperature of 27 C.

In the following section, Equation 4 is derived from basic NMR principles and it is shown that the cross coupling between the static and applied magnetic field gradients is zero for the bi-polar PFG pulse spin-echo sequence shown in FIG. 4. The spin echo amplitude M(f) at time t in the presence of an applied field gradient can be written in the form (e.g., see R. F. Karlicek and I. J. Lowe, J. of Mag. Res., v 37, p. 78, 1980).

$$\ln\left(\frac{M(t)}{M_0(t)}\right) = -D\gamma^2 \left[ \int_0^t \left( \int_0^{t'} G_{eff}(t'')dt'' \right)^2 dt' \right] \quad (5)$$

where $M_0(f)$ is the spin echo amplitude at time t in the absence of the applied field gradient, D is the diffusion constant, γ is the gyromagnetic ratio of the nuclear spins, and $G_{eff}$ is the effective gradient in each time interval in the bipolar PFG sequence. Eq. 5 shall be used to derive Eq. 4 for the echo amplitude in the bi-polar sequence shown in FIG. 4. The effective gradient in Eq. 5 is the algebraic sum of the applied and static field gradients.

The first step in calculating the logarithm of M(t) is to determine the effective gradients for each of the 10 time intervals of the bipolar PFG sequence shown in FIG. 4. The effective gradients are shown in FIG. 8. The re-forcing RF pulse effectively changes the polarity of the gradients as shown in FIG. 8. This is discussed in detail in the above-referenced paper by Karlicek and Lowe. The effective gradients in each time interval and their time integrals are shown in Table 3 of FIG. 9. The next step in computing the logarithm of the echo amplitude in Eq. 5 is to square the integrals of the effective gradients (column 4 of Table 3) and perform the remaining time integrals. The results are shown in Table 4 of FIG. 10 and Table 5 of FIG. 11. Note that the factor involving the negative product of the gyromagnetic ratio and the diffusion constant in Eq. 5 is not included in Tables 4 and 5. Table 4 shows the coefficients of the squares of the applied and static gradient terms that are derived from performing the double time integrations in Eq. 5. Table 5 shows the coefficients of the cross terms from each of the 10 integration intervals. By summing the contributions from the 10 time intervals in Tables 4 and 5 we obtain the result shown in Eq. 4. That is, one finds by summing the 10 intervals in Table 5 and performing the necessary algebra, that the coefficient of the product of the static and applied gradients is identically zero.

The invention has been described with reference to particular preferred embodiment, but variations within the scope of the invention will occur to those skilled in the art. For example, it will be understood that other and/or further pulse sequences using non-symmetrical polarity PFG pulses can be utilized. As on example, instead of the modified PFG CPMG sequence in the described embodiment, a modified PFG stimulated echo sequence, or any other suitable modified sequence, could be employed, consistent with the principles hereof.

What is claimed is:

1. For use in conjunction with a logging device downhole in an earth borehole, a method for determining a property of a substance in a downhole measurement region, comprising the steps of:
providing a static magnetic field having a static magnetic field gradient in the measurement region;
applying, in the measurement region, a pulse sequence that includes a tipping pulse, a re-focusing pulse, and a pulsed field gradient pulse train; wherein the pulsed field gradient pulse train includes a first portion and a second portion;
the first portion comprising a first pulse or set of pulses having a first polarity and a second pulse or set of pulses having a second polarity, the second polarity being opposite to the first polarity, and wherein the first portion occurs before the re-focusing pulse;
the second portion comprising a third pulse or set of pulses having the first polarity and a fourth pulse or set of pulses having the second polarity, and wherein the second portion occurs after the re-focusing pulse; and
receiving one or more spin echoes from the measurement region.

2. The method as defined by claim 1, further comprising the step of determining said property from said spin echoes.

3. The method as defined by claim 2, wherein said property comprises one or more diffusion constants of said substance.

4. The method as defined by claim 2, wherein said step of determining said property from said spin echoes comprises inverting to determine one or more diffusion constants of said substance.

5. The method as defined by claim 4, further comprising applying a correction factor in the inversion for the square of the static magnetic field gradient of said static magnetic field.

6. The method as defined by claim 5, wherein said correction factor is determined empirically beforehand.

7. The method as defined by claim 2, wherein said step of determining said property from said spin echoes comprises inverting to determine one or more relaxation times of said substance.

8. The method as defined by claim 7, further comprising applying a correction factor in the inversion for the square of the static magnetic field gradient of said static magnetic field.

9. The method as defined by claim 8, wherein said correction factor is determined empirically beforehand.

10. The method as defined by claim 1, wherein said measurement region comprises a sample chamber in said logging device, said sample chamber containing fluid.

11. The method as defined by claim 1, wherein said measurement region comprises a region of formations surrounding the earth borehole.

12. The method as defined by claim 1, wherein said measurement region comprises a region in the earth borehole.

13. The method as defined by claim 1, wherein said pulsed field gradient pulses of a first polarity have a positive polarity, and said pulsed field gradient pulses of a second polarity have a negative polarity.

14. The method as defined by claim 1, wherein said pulsed field gradient pulses are applied in the following order of polarities: plus, minus, plus, minus.

15. The method as defined by claim 1, wherein said pulsed field gradient pulses are applied in the following order of polarities: minus, plus, minus, plus.

16. The method as defined by claim 1, wherein said applying of a tipping pulse and a refocusing pulse comprises applying a 90 degree RF tipping pulse and a 180 degree RF refocusing pulse.

17. The method as defined by claim 16, further comprising applying additional 180 degree refocusing pulses.

18. The method as defined by claim 1, wherein said pulse sequence comprises a modified PFG CPMG sequence.

19. The method as defined by claim 1, wherein said pulse sequence comprises a modified PFG stimulated echo sequence.

20. For use in conjunction with a logging device downhole in an earth borehole, in which a method is employed for determining a property of a substance in a downhole measurement region, including the following steps:

providing a static magnetic field in the measurement region having a static magnetic field gradient; applying, in the measurement region, a pulse sequence that includes RF pulses and pulsed field gradient pulses, said pulsed field gradient pulses including pulsed field gradient pulses of a given polarity; and receiving one or a plurality of spin echoes from the measurement region; the improvement comprising:

applying corrective pulses in said pulse sequence to obtain cancellation of a component of the spin echoes that depends on the magnitude and direction of the static magnetic field gradient of said static magnetic field.

21. The method as defined by claim 20, wherein said corrective pulses comprise further pulsed field gradient pulses having a polarity opposite to that of said given polarity.

22. The method as defined by claim 20, wherein said property comprises one or a plurality of diffusion constants.

23. The method as defined by claim 22, wherein said property is determined from said spin echoes by inversion, and further comprising applying a correction factor in the inversion for the square of the static magnetic field gradient of said static magnetic field.

* * * * *